United States Patent [19]
Johnson et al.

[11] Patent Number: 5,981,204
[45] Date of Patent: *Nov. 9, 1999

[54] METHOD FOR FORENSICALLY SCREENING HAIR SAMPLES FOR THE PRESENCE OF CANNABINOIDS

[76] Inventors: Ted Donald Johnson, 5239 Martingale Ave., Las Vegas, Nev. 89119; W. Craig Brown, 3417 Baldoyle La., Las Vegas, Nev. 89129; Raymond C. Kelly, 3302 E. Oquendo Rd., Las Vegas, Nev. 89120

[*] Notice: This patent is subject to a terminal disclaimer.

[21] Appl. No.: 08/851,733

[22] Filed: May 6, 1997

[51] Int. Cl.$^6$ .............................. G01N 33/53; G01N 1/00
[52] U.S. Cl. ..................... 435/7.92; 435/7.9; 435/7.1; 436/174
[58] Field of Search ................... 435/7.92, 7.1, 435/975; 436/901, 815, 174, 175, 176

[56] References Cited

U.S. PATENT DOCUMENTS

| | | |
|---|---|---|
| 3,623,950 | 11/1971 | Monsheimer et al. . |
| 3,966,551 | 6/1976 | Monsheimer et al. . |
| 3,986,926 | 10/1976 | Monsheimer et al. . |
| 5,324,642 | 6/1994 | Baumgartner . |
| 5,326,708 | 7/1994 | Lewis . |
| 5,354,654 | 10/1994 | Ligler et al. ................... 435/5 |
| 5,466,579 | 11/1995 | Baumgartner ............... 435/7.1 |
| 5,532,131 | 7/1996 | Lewis ........................ 435/7.9 |

FOREIGN PATENT DOCUMENTS

| | | |
|---|---|---|
| 2004068 | 6/1990 | Canada . |
| WO 90/01023 | 2/1990 | European Pat. Off. ......... 530/343 |
| WO900102 | 2/1990 | WIPO . |

OTHER PUBLICATIONS

Single Step™ Pharmadiagnostic Elisa Test Kit Insert; Diagnostix, Inc.; 7 pages.

Drug abuse screening with immunoassays: unexpected corss–reactivities and other pitfalls, by Colbert; British Journal Of Biomedical Science 1994; 51:136–146.

A research note: the outcome of GC/MS/MS confirmation of hair assays on 93 cannabinoid(+) cases, by Mieczkowski Forensic Science International 79(1995) 83–91.

Immunoassays of Amphetamines: Immunogen Structure vs Antibody Specificity, by Suttijitpalsai et al.; Asian Pacific Journal of allergy and Immunology (1992) 10:159–164.

Enzyme Immunoassay for Methamphetamine; Aoki and Kuroiwa; J. Pharm Dyn., 6, (1983) 33–38.

Comparison of quantitative results of drugs in human hair by GC/MS; Sachs & Raff; Forensic Science International; 61 (1993) 207–216.

Hair analysis, a novel tool in forensic and biomedical sciences: new chromatographic and electrophoretic/Elektrokinetic analytical strategies; J. of Chromatography B 689 (1997) 261–271.

Simultaneous quantification of opieates, cocaine and cannabinoids in hair; Forensic Science Internaitonal; 70 (1995) 165–174.

Methods for Assessing Drug Use Prevalence in the Workplace: A Comparison of Self–Report, Urinalysis, Cook, et al.; The Inyternational J. of the Addictions, 30(4), (1995) 403–426.

C. Jurado et al., Forensic Sci. Inter. 70: 165–170, 1995.

J. Segura. In: Hair Analysis in Forensic Toxicology, Proceedings of the International Conference and Workshop, Abu Dhabi Police, (Eds) RA de Zeeuw et al. Nov. 19–23. Forensic Science Labs., General Directorate of Abu Dhabi Police, Abu Dhabi, p. 351, 1995.

EM. Ostrea et al. Clin. Perinatol. 18: 629–645, 1991.

*Primary Examiner*—James C. Housel
*Assistant Examiner*—S. Devi
*Attorney, Agent, or Firm*—Quirk & Tratos

[57] ABSTRACT

A method and a buffer solution are set forth for testing for cannabinoid analytes extracted form a hair sample using enzyme linked immunosorbant assay (ELISA). The method includes preparation of a hair extract cocktail using an inorganic base and aliphatic alcohol and thereafter adding the buffer according to the present invention including at least one of (a) a phosphate buffer, (b) proteinaceous substance, (c) a non-ionic surfactant and (d) a polyhydric alcohol. The buffered solution is evaporated and analyzed using ELISA. By using ELISA to determine clearly negative samples, expensive confirmatory testing can be reserved for only those samples determined to be not clearly negative.

9 Claims, No Drawings

METHOD FOR FORENSICALLY SCREENING HAIR SAMPLES FOR THE PRESENCE OF CANNABINOIDS

FIELD OF THE INVENTION

The present invention relates to forensically acceptable methods for testing samples of hair to determine the presence of indicators of cannabinoid use and to compositions for use in such methods.

BACKGROUND OF THE INVENTION

Testing of hair samples for the presence of indicators of drug use has gained importance not only for evidence gathering for criminal justice system proceedings but in pre-employment and post-employment screening of individuals. Unlike urine or blood sample testing which can provide only short term information concerning drug use by the tested individual and can therefore produce a negative result through abstention preceding the taking of the sample, hair testing can provide a long-term history of drug use for periods of, for example, ninety days or more preceding the taking of the sample. For this reason hair testing for drug use has become a reliable and important pre-employment or periodic test which cannot be defeated by short term abstention.

Heretofore testing of hair samples for drug use of marijuana by looking for cannabinoids such as tetrahydrocannabinol (THC) has been through techniques such as gas chromatography-mass spectrometry (GC/MS) and tandem gas chromatography-mass spectrometry (GC/MS/MS). These techniques not only qualitatively produce data indicative of the presence or absence of indicators of drug use from a hair sample but also quantify those results. These tests are expensive and time consuming. What is needed is a relatively fast and economical screening test which identifies clearly negative samples, i.e. samples with less than predetermined threshold amounts of cannabinoids, from samples which are positive or not clearly negative. By performing a screening test of the samples, the necessity of performing complicated, expensive and time consuming assays including GC/MS or GC/MS/MS on determined negative samples would be obviated. Such assays would be reserved for those samples which, by the screening test, were either presumptively positive or otherwise not clearly identifiable as negative. Reserving the use of these assays to samples which are not identified by the screening test as clearly negative would result in savings in time and manpower for the laboratory providing the testing.

For radioimmunoassay, there is presented a problem of use and disposal of the radioactive isotope used in the assay.

An appropriate screening test, any such test is one which is forensically sustainable in its own right and accordingly must use generally accepted scientific techniques and principles.

Enzyme linked immunosorbant assay (ELISA) has been used for analyzing urine and blood samples to determine the presence of cannabinoids. ELISA is, compared to the other assay methods such as GC/MS and GC/MS/MS, relatively inexpensive, fast and accurate to quantitatively determine the presence of cannabinoid analytes indicative of use of marijuana. However, attempts to use ELISA as a screening test for cannabinoids in hair samples has heretofore been unsuccessful. ELISA relies upon immunospecific reactions of the analytes to test for the presence of substances. ELISA testing is well known, is described in U.S. Pat. No. 4,952,517 issued Aug. 28, 1990 and accordingly will not be described herein. It is believed that procedures heretofore used for obtaining and analyzing the hair extract containing cannabinoid analytes have been frustrated by adherence of these analytes or unknown amounts thereof on analytical surfaces resulting in the inability to correlate the results of the assay with the actual presence or absence of the analytes being tested for. Accordingly ELISA has not been successful as a test for cannabinoid analytes extracted from hair samples.

SUMMARY OF THE INVENTION

There is set forth, according to the present invention, a method for testing for cannabinoid analytes extracted from a hair sample using ELISA and a buffer solution to accomplish the same.

Toward this end the method generally is directed to preparation of a chemically stable "cocktail" hair extract which contains cannabinoid analytes in such a manner that the cocktail is susceptible to analysis by ELISA to determine the quantities of cannabinoid analytes in the extract or whether the cannabinoid concentration is above a predetermined threshold amount.

The method includes preparation of the cocktail for ELISA analysis by introducing to a known quantity of hair sample a liquid mixture of an inorganic base and aliphatic alcohol and incubating the mixture to extract cannabinoid analytes from the hair into the solution. After incubation, the buffer solution according to a further aspect of the present invention is added, the buffer including at least one of (a) a phosphate buffer, (b) proteinaceous substance, (c) a non-ionic surfactant and (d) a polyhydric alcohol. Thereafter the method includes evaporating the alcohol of the mixture preferably in a nitrogen atmosphere. The extract containing the cannabinoid analytes is thereafter analyzed using enzyme linked immunosorbant assay (ELISA) specifically targeting for cannabinoids.

The method according to the present invention qualitatively determines the presence of cannabinoid compounds in the hair sample in concentrations ranging from $10^{-15}$ Gm (femtograms) to $10^{-12}$ Gm (picograms) per milligram of sample.

If the screening test results are positive or not clearly negative, other assays such as GC/MS and GC/MS/MS can be used to unequivocally identify and measure the concentration of the target analyte.

The buffer for use in the method according to the present invention preferably is substantially 2.653 Gm $KH_2PO_4$, 3.8 Gm $Na_2HPO_4$, 1.0 gm bovine albumin, 100 mg Triton X or other suitable surfactant and 5 mL ethylene glycol (sterile) per liter of deionized water.

DESCRIPTION

The hair sample from the subject to be tested for cannabinoids is collected in the same manner as are hair samples for other types of assays, i.e. RIA, GC/MS and GC/MS/MS. The hair sample is collected from the subject and from the root end of the hair sample, the hair is cut to a length of 3.9 cm. Typically 3.9 cm of growth represents a history for the subject of approximately ninety days. The 3.9 cm length of hair is cut into small pieces of 1 to 2 mm long; the cut pieces are then mixed thoroughly. From the mixed pieces a weighed 20 mg portion of the cut hair is transferred into a test tube which is suitably labeled for testing for multiple drugs; a second 20 mg portion of hair is transferred to a second labeled test tube for the screening procedure according to the present invention. As disclosed in our co-pending application entitled "Forensically Acceptable Method For Screening Hair Samples For Indication Of Use Of Drugs Of Abuse", the hair for testing for multiple drugs and for testing according to the present invention may be incorporated into an overall system for preliminary screening of target analytes through a diversified series of immunoassays including ELISA and RIA to determine the presence or absence of target compounds in the hair samples. If positive preliminary results are obtained, GC/MS or GC/MS/MS assays may be used to measure, confirm and certify the amount of the target analyte present in the sample.

The remaining aliquot of the hair sample is retained for further confirmatory testing if required.

While as stated above, the hair sample in the test tube marked for multiple drug assay can be used for the diversified series of immunoassays described above, the present invention is directed to the second sample of hair which will be dedicated to the screening assay for cannabinoid analytes.

To the tube containing the hair sample to be tested for cannabinoids, 1 mL of 1% wash solution is added to wash the exterior of the hair to remove environmentally implicated compounds. The solution is preferably a mix of 10 mL of Nexus® clarifying treatment shampoo with 1 L of deionized water. After the hair sample and wash solution is left standing for 10 minutes at room temperature, the tube is swirled and the liquid is decanted. 2 mL of deionized water are added, the tube is swirled and the liquid decanted immediately. The washing with the deionized water is repeated again.

After washing of the hair sample, 1 ml of acetone is added to the tube, left standing 5 minutes for room temperature, the tube swirled and dumped. The foregoing washing steps prepare the hair sample for extraction of cannabinoid analytes according to the method of the present invention.

The cannabinoid analytes of the hair sample are extracted by adding an extraction solution consisting of a mixture of an inorganic base and an aliphatic alcohol, preferably 0.1% (v/v) ammonium hydroxide in methanol. For a 20 mg hair sample it has been found that 2 mL of the extraction solution is sufficient. After the extraction solution has been added, the mixture is incubated to promote extraction of the cannabinoid analytes from the hair sample. Preferably according to the method of the present invention, incubation consists of heating the test tube at 70° to 75° C. for 2 hours.

Subsequent to incubation, the test tube is cooled and the liquid extract of the tube is transferred to one or more 12×75 mm test tubes. The original test tubes and hair are discarded. To each of these test tubes a blocking buffer solution according to the present invention is added. The buffer solution includes at least one of a phosphate buffer, proteinaceous substance, non-ionic surfactant and a polyhydric alcohol. Preferably the blocking buffer solution is prepared by adding to a 1 L flask the following: 2.653 Gm of $KH_2PO_4$, 3.800 Gm $Na_2HPO_4$, 1.0 Gm bovine albumin, 100 mg Triton X and 5 mL ethylene glycol (sterile) per liter of deionized water. The solution is diluted to 1 L with distilled water and mixed. The solution should be checked to determine that the pH is 7.0±0.5. The prepared buffer solution can be stored under refrigeration for limited periods of time at between 2° to 8° C. Approximately 25 μL of the blocking buffer is added to each of the 12×75 mm test tubes containing the hair extracts.

Thereafter, the methanol of the hair extract solution and buffer solution is evaporated preferably under a stream of dry nitrogen at 55° C. The nitrogen preferably is set at a pressure no greater than 3.5 psia.

CONTROLS AND CALIBRATORS

To control and calibrate for ELISA, a calibrator tube is provided and into which is added 150 μL of ELISA THC calibrator containing 6 ng per mL of delta-9-THC. This calibrator will serve to provide a known concentration of cannabinoid analytes (THC) for calibrating ELISA. To the tube containing the ELISA THC screen calibrator is added approximately 25 μL of the buffer solution described above. The methanol is thereafter evaporated under dry nitrogen at 55° C. and at a pressure of no more than 3.5 psia. To the calibrator tube, after evaporation is added 2,160 μL of 46 mM phosphate buffer, (pH 7). After the addition of the phosphate buffer, the calibration solution is prepared.

To serve as controls, there are also provided ELISA THC screen low and high controls. The low control contains user hair previously assayed to contain 3 to 10 picograms of THC per mg of hair. The high control contains user hair previously assayed to contain 40 to 100 picograms of THC per mg of hair. These low control and high control samples are extracted according to the method described above in reference to the test samples.

THE ELISA TEST

The ELISA assay of the test sample, control samples and calibrator is in accordance with the instructions provided with ELISA plates kits for THC which can be obtained from, for example, Diagnostix, Ltd 4730 Coopers Avenue, #27, Mississaugua, Ontario, Canada which are used for urine and/or blood samples. A robotic pipettor can be preprogrammed to run the analyses of numerous test samples as well as controls as is well known in the art.

The test sample, control samples and calibrator are pipetted into the ELISA wells along with a kit provided enzyme conjugate. The samples are incubated for approximately 60 minutes at room temperature. During the incubation period the enzyme conjugate competes with the analytes in the sample for binding sites on an analyte targeting antibody coated in the ELISA well.

After incubation, the samples are decanted from the wells and the wells are washed as by submerging the ELISA plate in a water bath. The washing water is removed from the wells.

Thereafter approximately 100 μL of enzyme conjugate is added to each well and the plate is incubated for 30 minutes. After the aforesaid incubation period, the conjugate is decanted, the plates are washed with water and the wells are thereafter washed approximately 6 times with a wash buffer typically supplied with the ELISA plate kit. 100 μL of a substrate reagent, also supplied with the ELISA kit, is added to each well and the plates are incubated for 20 to 30 minutes in the dark at room temperature until the color in the wells appears developed. The development of the color by addition of the substrate reagent is inversely proportional to the concentration of the targeted analyte. That is, a darker color indicates a lower concentration.

After the incubation period, 100 mL of kit supplied stopping reagent is added to each well. A plate reader which optically reads the color concentration of the well is used to read the test results and is typically set at wavelengths of 450 nm and 630 nm. Scanning the calibrator and control samples serves as a control for the reading of the analyses since these controls have known amounts of the targeted analyte.

It has been found that by using the method and the buffer solution described above, the screening test using ELISA can qualitatively determine the presence of cannabinoid compounds in a hair sample in concentration ranges from femtograms to picograms per milligram of sample. Furthermore the screening analyses using ELISA is economical when compared to other assays such as GC/MS or GC/MS/MS due to savings of time, manpower and equipment. By using the ELISA screening test, clearly negative samples need not be subjected to the complicated assays thereby saving these expensive procedures and equipment for confirmatory assays of positive or marginal tests.

While we have described certain embodiments of the method for forensically analyzing hair samples for the presence of cannabinoids and a buffer for use therein, it is to be understood that the invention is subject to modifications without departing from the spirit and scope of the claims herein.

We claim:

1. A method for testing a sample of hair for the presence of cannabinoid analytes using an enzyme-linked immunosorbent assay test kit for tetrahydrocannabinol (THC) comprising:
   (i) adding a mixture of an inorganic base and aliphatic alcohol to the sample, said inorganic base being in a concentration of approximately 0.1% in said alcohol;
   (ii) incubating the mixture and sample thereby releasing said analytes into the mixture solution;
   (iii) introducing to the mixture and sample a non-specific buffer solution including at least one of (a) a phosphate buffer, (b) a serum protein, (c) a non-ionic surfactant and (d) a polyhydric alcohol;
   (iv) evaporating the aliphatic alcohol and the polyhydric alcohol, if any, of the mixture and buffer solution in a nitrogen atmosphere; and
   (v) analyzing the resulting material from steps (i) through (iv) using the enzyme linked immunosorbent assay (ELISA) test kit.

2. The method of claim 1 wherein the adding step includes adding ammonium hydroxide as the inorganic base.

3. The method of claim 1 wherein adding step includes adding methanol as the aliphatic alcohol.

4. The method of claim 1 wherein the adding step includes adding ammonium hydroxide as the inorganic base and methanol as the aliphatic alcohol.

5. The method of claim 4 wherein the adding step comprises adding 0.1% ammonium hydroxide in methanol.

6. The method of claim 1 wherein the introducing step includes introducing a buffer solution comprising (a) a phosphate buffer selected from the group consisting of potassium phosphate and sodium phosphate, (b) a serum protein, (c) a non-ionic surfactant and (d) ethylene glycol.

7. The method of claim 6 wherein said introducing step includes introducing a buffer solution substantially consisting of 2.653 gm $KH_2PO_4$, 3.8 gm $Na_2HPO_4$, 1.0 gm bovine albumin, 100 mg of a non-ionic surfactant and 5 ml ethylene glycol per liter of deionized water.

8. A method for testing a sample of hair for the presence of cannabinoid analytes using an enzyme linked immunosorbent assay test kit for tetrahydrocannabinol (THC) comprising:
   (i) adding a mixture of an inorganic base and an aliphatic alcohol to the sample, said inorganic base being in a concentration of approximately 0.1% in said alcohol;
   (ii) incubating the mixture and sample thereby releasing said analytes into the mixture solution;
   (iii) introducing to the mixture obtained from step (ii) a buffer solution comprising (a) a phosphate buffer selected from the group consisting of potassium phosphate and sodium phosphate, (b) a serum protein, (c) a non-ionic surfactant and (d) ethylene glycol;
   (iv) evaporating the alcohol and ethylene glycol from the mixture and buffer solution obtained from step (iii) in a nitrogen atmosphere; and
   (v) analyzing the resulting material from steps (i)–(iv) using the enzyme linked immunosorbent assay (ELISA) test kit.

9. A method for testing a sample of hair for the presence of cannabinoid analytes using an enzyme-linked immunosorbent assay test kit of tetrahydrocannabinol (THC) comprising:
   (i) adding a mixture of an inorganic base and an aliphatic alcohol to the sample, said inorganic base being in a concentration of approximately 0.1%;
   (ii) incubating the mixture and sample thereby releasing said analytes into the mixture solution;
   (iii) introducing a buffer solution substantially consisting of 2.653 gm $KH_2PO_4$, 3.8 gm $Na_2HPO_4$, 1.0 gm bovine albumin, 100 mg of a non-ionic surfactant and 5 mL ethylene glycol per liter of deionized water;
   (iv) evaporating the alcohol of the mixture and buffer solution of step (iii) in a nitrogen atmosphere; and
   (v) analyzing the resulting mixture and buffer solution from step (iv) using the enzyme-linked immunosorbent assay (ELISA) test kit.

* * * * *